US008083780B2

(12) United States Patent
McClellan, III et al.

(10) Patent No.: US 8,083,780 B2
(45) Date of Patent: Dec. 27, 2011

(54) SPINAL FIXATION MECHANISM (75) Inventors: John McClellan, III, Omaha, NE (US);
Kevin Sichler, West Orange, NJ (US);
Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 289 days.

(21) Appl. No.: 12/428,613

(22) Filed: Apr. 23, 2009

(65) Prior Publication Data
US 2010/0274291 A1 Oct. 28, 2010

(51) Int. Cl.
*A61B 17/70* (2006.01)
(52) U.S. Cl. ......... 606/279; 606/277; 606/324; 606/330
(58) Field of Classification Search .......... 606/246–279, 606/324, 330; 623/17.11–17.16
See application file for complete search history.

(56) References Cited

U.S. PATENT DOCUMENTS

| | | | | | |
|---|---|---|---|---|---|
| 4,274,401 | A | * | 6/1981 | Miskew | 606/276 |
| 6,139,548 | A | * | 10/2000 | Errico | 606/252 |
| 6,261,288 | B1 | * | 7/2001 | Jackson | 606/250 |
| 7,806,894 | B1 | * | 10/2010 | Rosenblatt et al. | 606/47 |
| 2002/0040223 | A1 | * | 4/2002 | Sato et al. | 606/61 |
| 2002/0169451 | A1 | * | 11/2002 | Yeh | 606/61 |
| 2003/0032959 | A1 | * | 2/2003 | Yeh | 606/61 |
| 2003/0187437 | A1 | * | 10/2003 | Ginsburg | 606/61 |
| 2004/0260286 | A1 | * | 12/2004 | Ferree | 606/61 |
| 2005/0080416 | A1 | * | 4/2005 | Ryan et al. | 606/61 |
| 2007/0093832 | A1 | * | 4/2007 | Abdelgany | 606/61 |
| 2007/0233068 | A1 | * | 10/2007 | Bruneau et al. | 606/61 |
| 2008/0058806 | A1 | * | 3/2008 | Klyce et al. | 606/61 |
| 2008/0114401 | A1 | * | 5/2008 | Liu et al. | 606/276 |
| 2011/0166601 | A1 | * | 7/2011 | Cain | 606/263 |

* cited by examiner

*Primary Examiner* — Eduardo C Robert
*Assistant Examiner* — Ellen C. Hammond
(74) *Attorney, Agent, or Firm* — Rahman LLC

(57) ABSTRACT

A mechanism for fixing a spinal support to vertebrae includes a support member and a pedicle screw component. The support member comprises an elongated end comprising a longitudinal axis. A hook connects to the elongated end and receives the vertebrae. The hook is angled in three different planes with respect to the longitudinal axis. A connector section connects the elongated end to the hook and is angled with respect to the elongated end and comprises a thickness less than a thickness of the elongated end. The pedicle screw component comprises a fixation component anchored in the vertebrae. The fixation component comprises a socket; a screw head comprising a bulbous end that fits into the socket; and a channel that receives the elongated end. A pin causes outward expansion of the bulbous end; and a blocking mechanism is attached to the screw head and adjacent to the elongated end.

21 Claims, 8 Drawing Sheets

SPINAL FIXATION MECHANISM

BACKGROUND

1. Technical Field

The embodiments herein generally relate to spinal fixation devices, and, more particularly, to devices for preventing slippage between hook and vertebrae and methods of preventing slippage using the same.

2. Description of the Related Art

A unilateral or bilateral stress fracture of the narrow bridge between the upper and lower pars interarticularis is a common cause of lower back pain in adolescent athletes. A variety of surgical treatments have been used, including posterior fusion and posterolateral fusion, to address symptomatic spondylolysis. Moreover, there are many known spinal conditions that require imposition and/or maintenance of corrective forces on the spine in order to return the spine to its normal condition. As a result, numerous devices have been developed for use in spinal fixation. One such type of spinal fixation device generally includes one or more spinal rods placed parallel to the spine with fixation devices, such as hooks, screws, or plates, interconnected between the spinal rods and selected portions of the spine. Spinal fixation devices are used to correct problems in the lumber and thoracic portions of the spine, and are often installed posterior to the spine on opposite sides of the spinous process and adjacent to the transverse process. Conventional spinal fixation devices include a spinal rod connected to the spine using a hook which engages a portion of vertebrae. It is necessary for such spinal fixation devices to secure the vertebrae within the hook in order to ensure that the spinal rod remains correctly in place both during and after surgery.

Typically, spinal fractures and scoliosis have been treated with the use of distraction rods, such as the type known as Harrington rods, having hooks for engagement with vertebrae above and below the damaged spinal section. In most instances such hooks are capable of rotation about the rod, and are maintained at the desired angular orientations merely by the frictional resistance of screws located above and below the hook. Such mechanisms are relatively insecure and under high axial load the hooks tend to swing on the rod, and thus become disengaged from the vertebrae. One solution to this problem is the so-called Moe rod which has a square cross section, to which a matching cross section is provided in the hook openings. In this alternative, however, when the rod is bent (as it often must be) extreme care must be taken to bend it in the desired plane relative to the plane of the hooks, since no rotational adjustment of the hooks on the rod is possible. Precise bending is often difficult to achieve.

SUMMARY

In view of the foregoing, an embodiment herein provides a device for fixing a spinal support to vertebrae, wherein the device comprises an elongated end comprising a longitudinal axis; a hook connected to the elongated end in which the vertebrae is received, wherein the hook is angled in three different planes with respect to the longitudinal axis; and a connector section that connects the elongated end to the hook, wherein the connector section is angled with respect to the elongated end and comprises a thickness less than a thickness of the elongated end. Preferably, the hook comprises an elbow connector defining a recess for receiving the vertebrae. Moreover, the hook may comprise a gripping portion comprising serrated teeth positioned adjacent to the elbow connector. Additionally, the hook may comprise a head section having a width greater than a width of each of the elongated end and the connector section. Furthermore, any of the elongated end and the head section may comprise a hole configured therethrough. Also, the device may further comprise a ring member encircling the connector section. Preferably, the head section is angled with respect to the elongated end, the elbow connector is angled with respect to the head section, and the gripping portion is angled with respect to the elbow connector.

Another embodiment provides an apparatus for fixing a spinal support to vertebrae, wherein the apparatus comprises a support member and a pedicle screw component. The support member comprises an elongated end comprising a longitudinal axis; a hook connected to the elongated end in which the vertebrae is received, wherein the hook is angled in three different planes with respect to the longitudinal axis; and a connector section that connects the elongated end to the hook, wherein the connector section is angled with respect to the elongated end and comprises a thickness less than a thickness of the elongated end. The pedicle screw component comprises a fixation component anchored in the vertebrae, wherein the fixation component comprises a socket; a screw head comprising an expandable outwardly protruding bulbous end that fits into the socket; and a channel that receives the elongated end of the support member. The pedicle screw component further comprises a pin positioned through the bulbous end causing outward expansion of the bulbous end; and a blocking mechanism attached to the screw head and adjacent to the elongated end of the support member.

Preferably, the hook comprises an elbow connector defining a recess for receiving the vertebrae. Additionally, the hook may comprise a gripping portion comprising serrated teeth positioned adjacent to the elbow connector. Furthermore, the hook may comprise a head section having a width greater than a width of each of the elongated end and the connector section. The support member may comprise a hole configured therethrough. Also, the support member may further comprise a ring member encircling the connector section. Moreover, the head section is preferably angled with respect to the elongated end, the elbow connector is preferably angled with respect to the head section, and the gripping portion is preferably angled with respect to the elbow connector.

Another embodiment provides a method comprising anchoring a fixation component of a pedicle screw component to vertebrae, wherein the fixation component comprises a socket; attaching an expandable outwardly protruding bulbous end of a screw head into the socket; inserting a pin through the bulbous end; and positioning a support member onto the vertebrae, wherein the support member comprises an elongated end comprising a longitudinal axis; a hook connected to the elongated end in which the vertebrae is received, wherein the hook is angled in three different planes with respect to the longitudinal axis; and a connector section that connects the elongated end to the hook, wherein the connector section is angled with respect to the elongated end and comprises a thickness less than a thickness of the elongated end. The method further comprises inserting the elongated end through the screw head; and attaching a blocking mechanism to the screw head to compress the elongated end against the pin causing the bulbous end to outwardly expand and lock into the socket, and causing the hook to compress against the vertebrae. Additionally, the method may further comprise creating a slot in the vertebrae; and attaching the hook in the slot. Moreover, the support member may further comprise a ring member encircling the connector section, wherein the method may further comprise applying pressure to the ring member and the screw head in order to move the hook closer to the screw head.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a spinal fixation device for preventing slippage between a hook and vertebrae and methods of preventing the slippage using the device. Referring now to the drawings, and more particularly to FIGS. 1(A) through 6, where similar reference characters denote corresponding features consistently throughout the figures, there are shown preferred embodiments.

FIGS. 1(A) through 1(D) illustrate schematic diagrams of a spinal fixation support member device 1 according to a first embodiment herein. The support member device 1 comprises an elongated end 2 comprising a longitudinal axis X; a hook 3 connected to the elongated end 2 in which a vertebrae 6 is received, wherein the hook 3 is angled in three different planes with respect to the longitudinal axis X; and a connector section 4 that connects the elongated end 2 to the hook 3, wherein the connector section 4 is angled with respect to the elongated end 2 and comprises a thickness less than a thickness of the elongated end 2. The device 1 is bendable/deformable, and, in one embodiment, comprises titanium. Furthermore, the hook 3 comprises an elbow connector 5 defining a recess 8 for receiving and holding the vertebrae 6. Additionally, the hook 3 comprises a gripping portion 9 comprising serrated teeth 10 positioned adjacent to the elbow connector 5. The recess 8 may be configured according to a variety of specifications. In this regard, in accordance with the embodiments herein, the angle associated with recess 8 may be configured smaller or larger than that shown in the drawings. For example, if the design specifications require a larger angle; i.e., gripping portion 9 to be angled away from the elongated end 2, then hook 3 may be bent 15-20 degrees medially, or at any other degree of angulation. Preferably, the gripping portion 9 is positioned in the center of the spinal canal rather than pointing into the lateral recess where the nerve sits. An angled connection 14 is positioned between the connector section 4 and the elongated end 2. This angled connection 14 allows the connector section 4 to have a smaller thickness than the elongated end 2. Moreover, this angled connection 14 creates a recess 15 between the elongated end 2 and the hook 3.

Moreover, the hook 3 comprises a head section 11 having a width greater than a width of each of the elongated end 2 and the connector section 4. The head section 11 is angled with respect to the elongated end 2, the elbow connector 5 is angled with respect to the head section 11, and the gripping portion 9 is angled with respect to the elbow connector 5 thereby allowing the hook 3 to be angled in three different planes with respect to the longitudinal axis X.

Figure 1A:
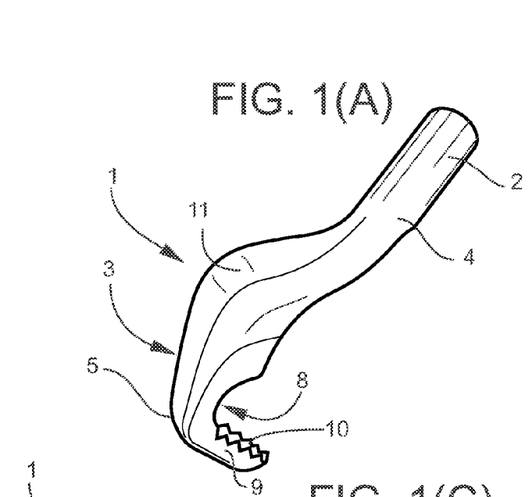
FIGS. 1(A) through 1(D) illustrate schematic diagrams of a spinal fixation device for preventing slippage between a hook and vertebrae therein according to a first embodiment herein.
Figure 1B:
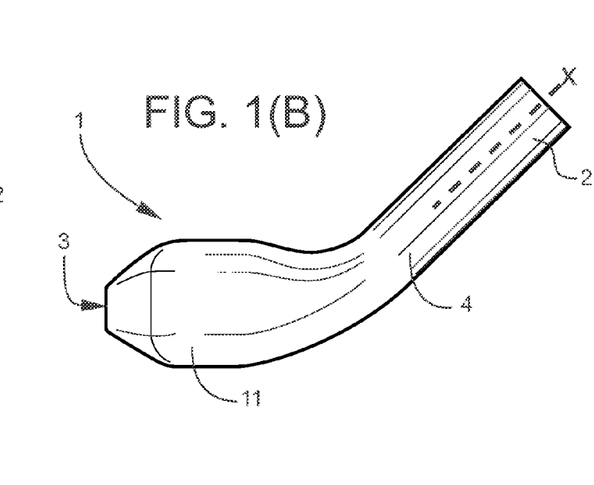
Figure 1C:
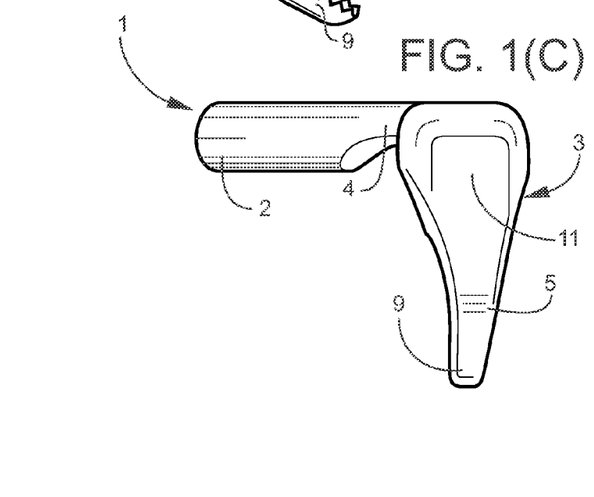
Figure 1D:
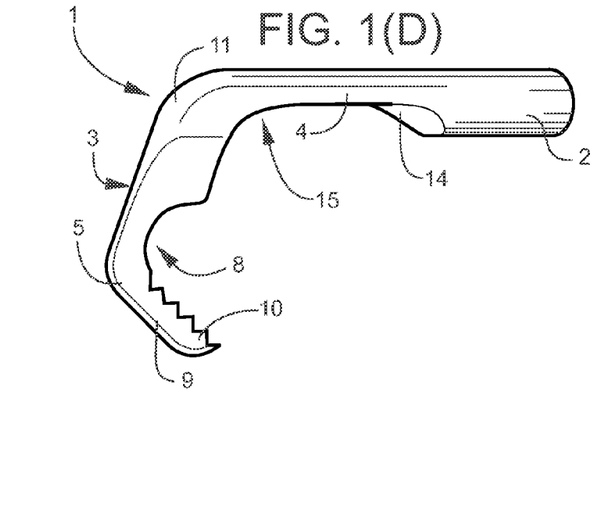
Figure 2A:
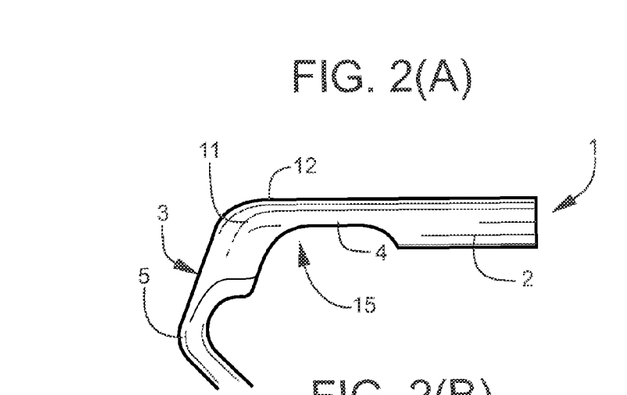
FIGS. 2(A) and 2(B) illustrate schematic diagrams of a spinal fixation device for preventing slippage between a hook and vertebrae therein according to a second embodiment herein.
Figure 2B:
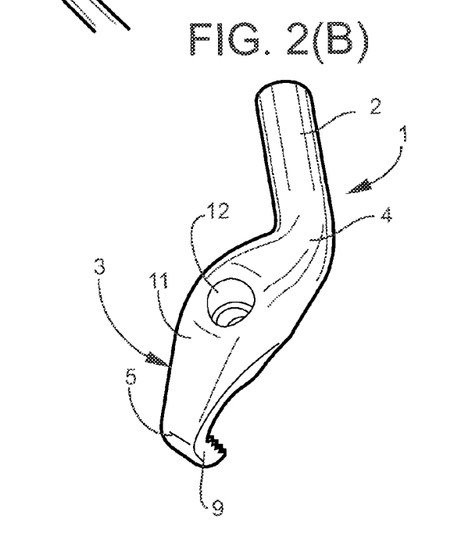

In one embodiment shown in FIGS. 2(A) and 2(B), the head section 11 comprises a hole 12 configured therethrough. The hole 12, which may comprise threads, is configured to receive a set screw (not shown). FIGS. 3(A) through 3(H) illustrate further embodiments including the device 1 of FIGS. 1 through 2(B) attached to a pedicle screw component 20 comprising a fixation component 25 anchored in the vertebrae 7, a screw head 21, a pin 35, and a blocking mechanism 30. The fixation component 25 comprises a socket 26, and the screw head 21 comprises an expandable outwardly protruding bulbous end 23 that fits into the socket 26; and a channel 28 that receives the elongated end 2 of the support member device 1. The pin 35 is positioned through the bulbous end 23 causing outward expansion of the bulbous end 23. The blocking mechanism 30 is attached to the screw head 21 and is adjacent to the elongated end 2 of the device 1. A set screw (not shown) inserted through the hole 12 of the device 1 in FIGS. 2(A) and 2(B) may be used to contact the underlying vertebrae 6 to provide further support thereof.

In accordance with FIGS. 1(A) through 5, the hook 3 is used for holding vertebrae 6, wherein the elongated end 2 that is set within the screw head 21 of the pedicle screw component 20 prevents slippage between the hook 3 and the vertebrae 6. The elongated end 2 of the device 1 may be embodied in any appropriately-sized configuration, and the gripping portion 9 may be configured in different embodiments other than serrated teeth 10 to properly capture, grab, or hook the vertebrae 6.

During use, the hook 3 slips under the inferior border of the lamina 7 in the interlaminar region. The elongated end 2 is placed in the screw head 21 of the pedicle screw. The hook can then be compressed against the undersurface of the lamina of the vertebrae while the rod is secured in the pedicle screw.

Tightening of the blocking mechanism 30 into the screw head 21 using any appropriate tightening mechanism fixes the elongated end 2 of the device 1 into place within the screw head 21 and allows the recess 8 of the hook 3 to be properly positioned around the vertebrae 6, which can then further secured using the set screw (not shown), if desired, to create a fixable arrangement with the vertebrae 6. To ensure proper seating, the elongated end 2 can be bent or deformed with a rod bender (not shown) or other similar device. Furthermore, the device 1 is configured to allow sufficient room for bone graft (not shown) to be placed between the device 1 and the lamina 7. For example, recess 15 between the elongated end 2 and the hook 3 allows for the inclusion of bone graft (not shown) material, which corrects a problem with conventional fixation techniques by allowing a surgeon more room for graft in the area of the spine/pars fracture.

While not shown, the fixation component 25 of the pedicle screw component 20 may be configured to include threads to create a fixable engagement with the vertebrae 6. Alternatively, the fixation component 25 may be configured with a tapered cavity and a substantially smooth shank containing no threading. Furthermore, the hook 3 may be configured in any of a number of types of hooks including large laminar, small laminar, thoracic laminar, and pedicle hooks, among others.

Figure 3A:
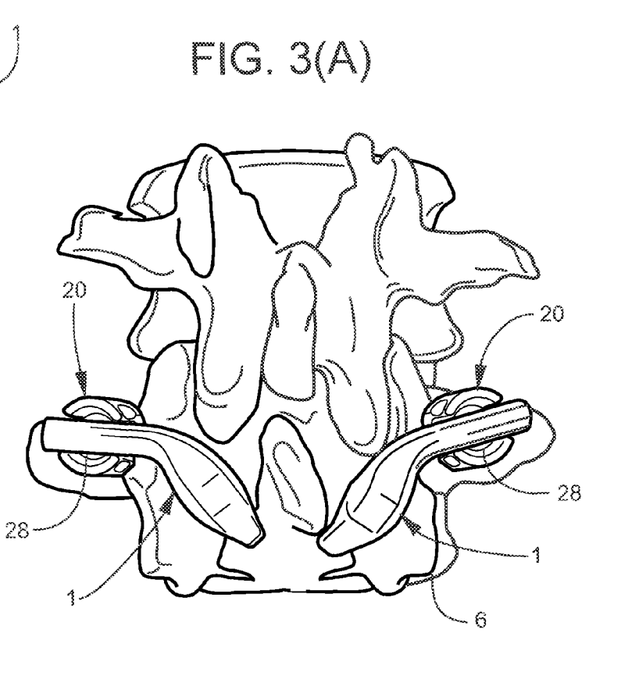
FIGS. 3(A) through 3(H) illustrate schematic diagrams of the device of FIGS. 1(A) through 1(D) attached to vertebrae according to an embodiment herein.
Figure 3B:
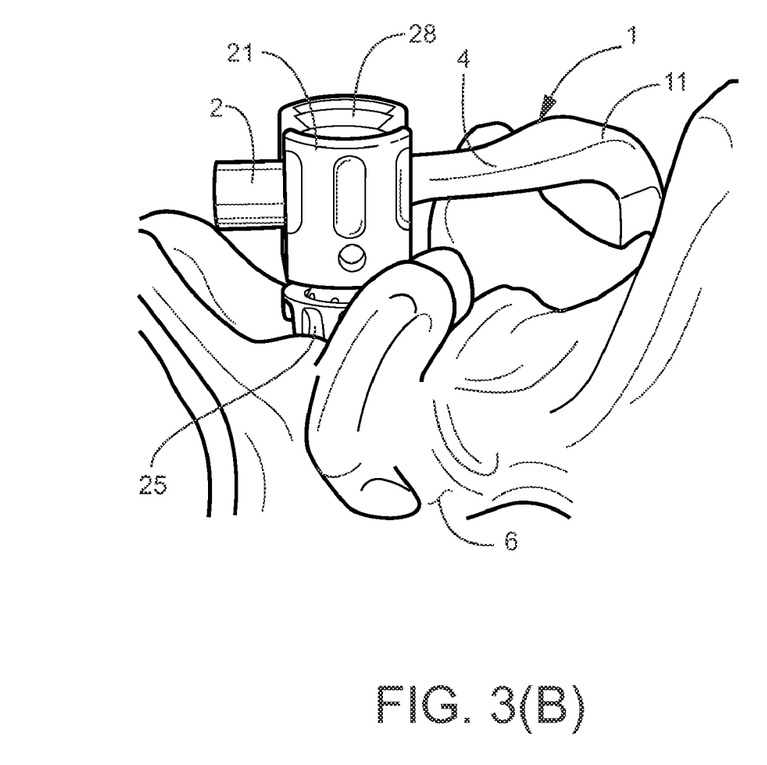
Figure 3C:
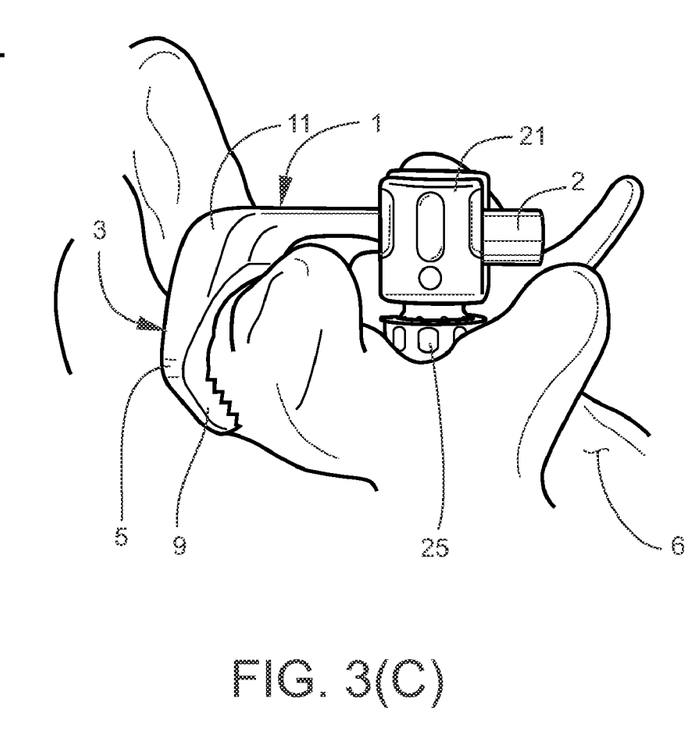
Figure 3D:
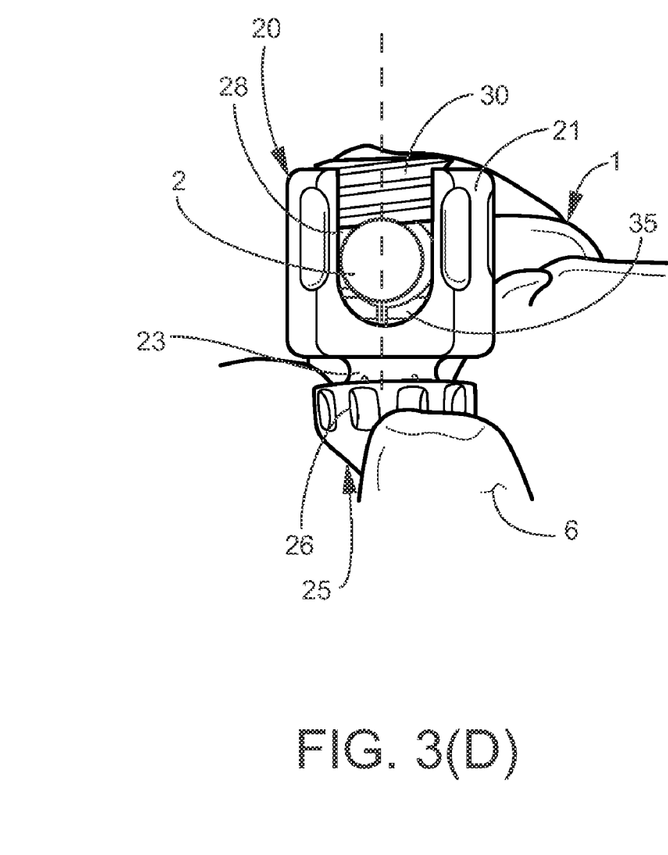
Figure 3E:
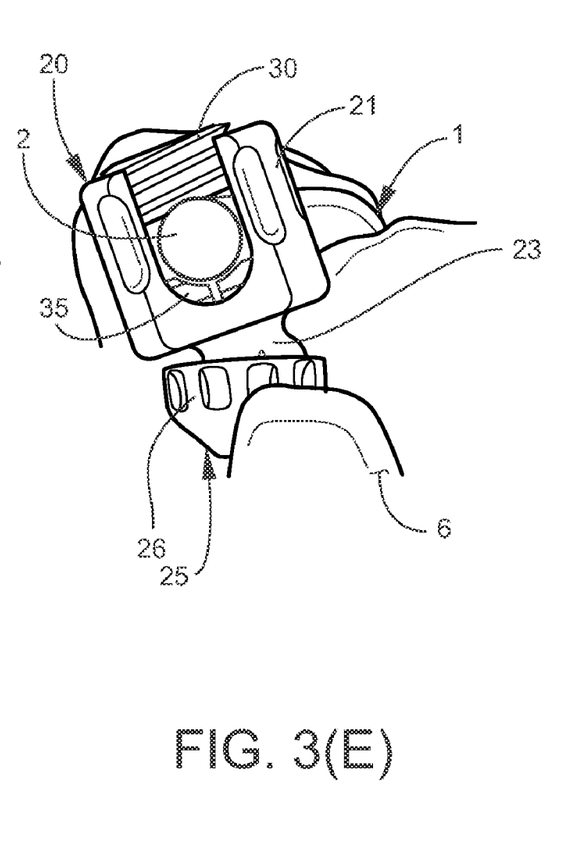
Figure 3F:
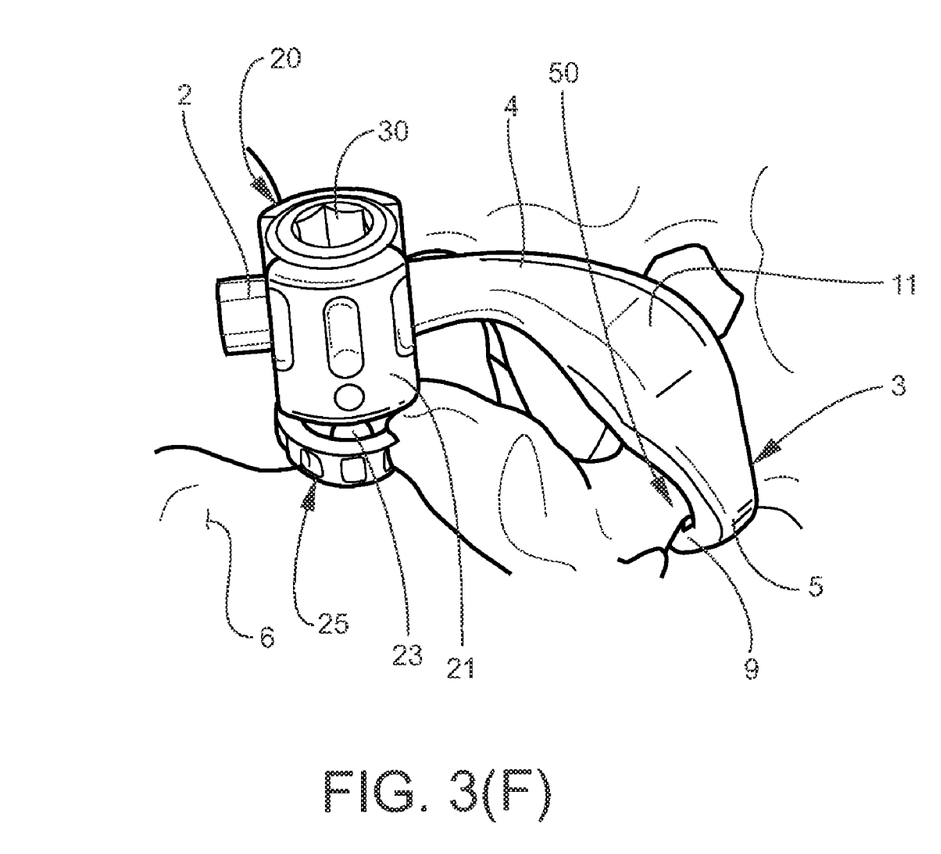

In one embodiment, the polyaxial characteristic of the pedicle screw component 20 is shown in FIGS. 3(D) and 3(E), wherein the screw head 21 is tilted with respect to the fixation component 25 thereby allowing the hook 3 to properly compress into the vertebrae 6. FIG. 3(F) illustrates the area of compression 50 on the vertebrae 6. The screw head 21 can be tilted in any direction so as to lock and/or compress the hook 3 into the vertebrae 6 to the maximum extent. Accordingly, this locking (i.e., once the blocking mechanism 30 is tightened) prevents any slippage between the hook 3 and the vertebrae 6.

Figure 3G:
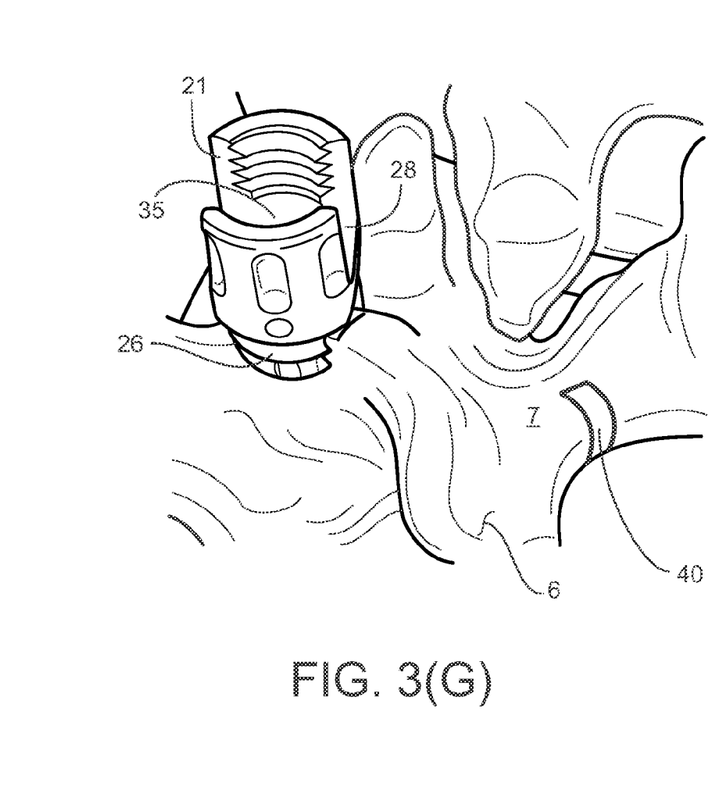
Figure 3H:
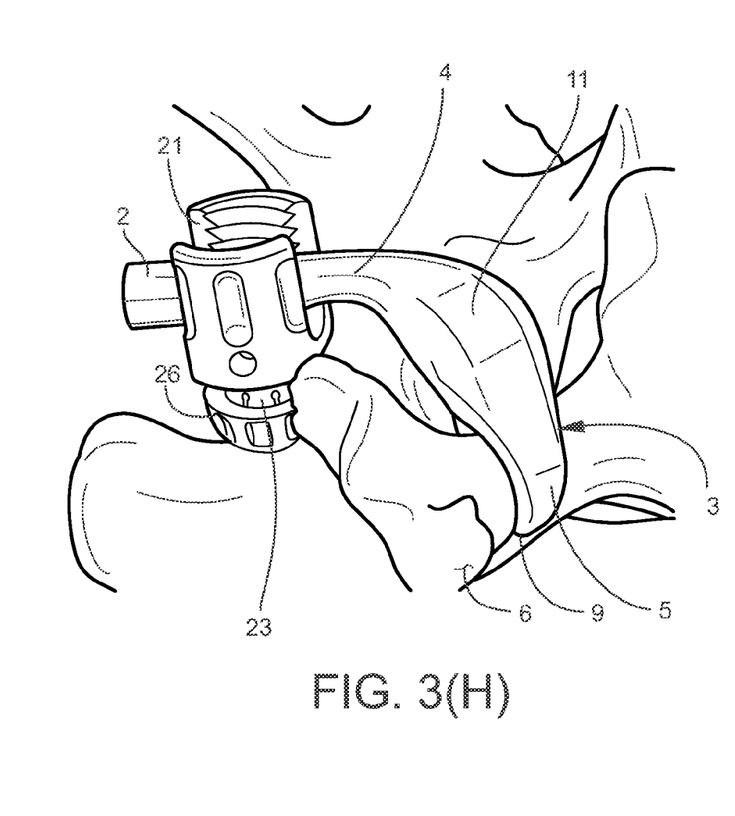

FIGS. 3(G) and 3(H), with reference to FIGS. 1(A) through 3(F), illustrates the hook 3 being seated in a bone slot 40 created in the vertebrae 6. In an embodiment, the bone slot 40 is created in the vertebrae 6 by nibbling the lamina 7 of the vertebrae 6 using a rongeur or a pituitary (not shown) or other appropriate device. The recess 8 of the hook 3 is then placed over the bone slot 40 to help the hook 3 achieve an improved grip over the vertebrae 6. The improved grip reduces the slippage between the hook 3 and the vertebrae 6 when compressed due to tightening of the blocking mechanism 30.

Figure 4:
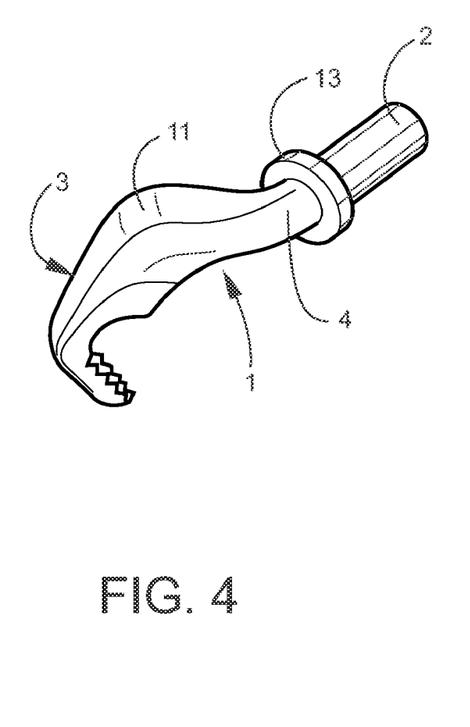
FIG. 4 illustrates a schematic diagram of a spinal fixation device for preventing slippage between a hook and vertebrae therein according to a third embodiment herein.
Figure 5:
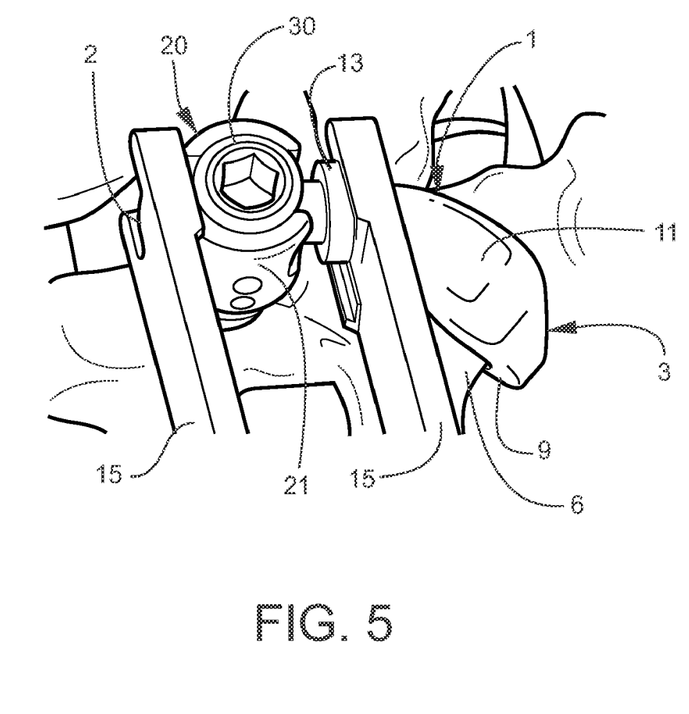
FIG. 5 illustrates a schematic diagram of the device of FIG. 4 attached to vertebrae according to an embodiment herein.

As shown in FIGS. 4 and 5, the device 1 may further comprise a ring member 13 encircling the connector section 4. In this embodiment, a compressor device 15 is used to compress the hook 3 into the vertebrae 6. Generally, the compressor device 15 engages the ring member 13 on one side and the elongated end 2 on the other side and then compresses the hook 3 into the vertebrae 6 for proper seating therein. Additionally, the compression diameter of the elongated end 2 can be adjusted through the compressor device 15. In this embodiment, the compressor device 15 is used to close the gap in the boney fracture before tightening the device 1 into the pedicle screw component 20. This is accomplished by pushing on ring member 13 opposite the screw head 21. In another embodiment, the elongated end 2 is configured much longer than that shown in the drawings with a hole (not shown) provided therethrough where the section of the elongated end 2 with the hole (not shown) therethrough protrudes past the screw head 21 and a distracter (not shown) that has a pin (not shown) on one side to mate with the hole (not shown) in the elongated end 2 and a flat side to mate with the screw head 21. Through a distraction motion, the hook 3 is pulled closer to the screw head 21 thereby closing the gap in the fracture before final tightening of the blocking mechanism 30.

Figure 6:
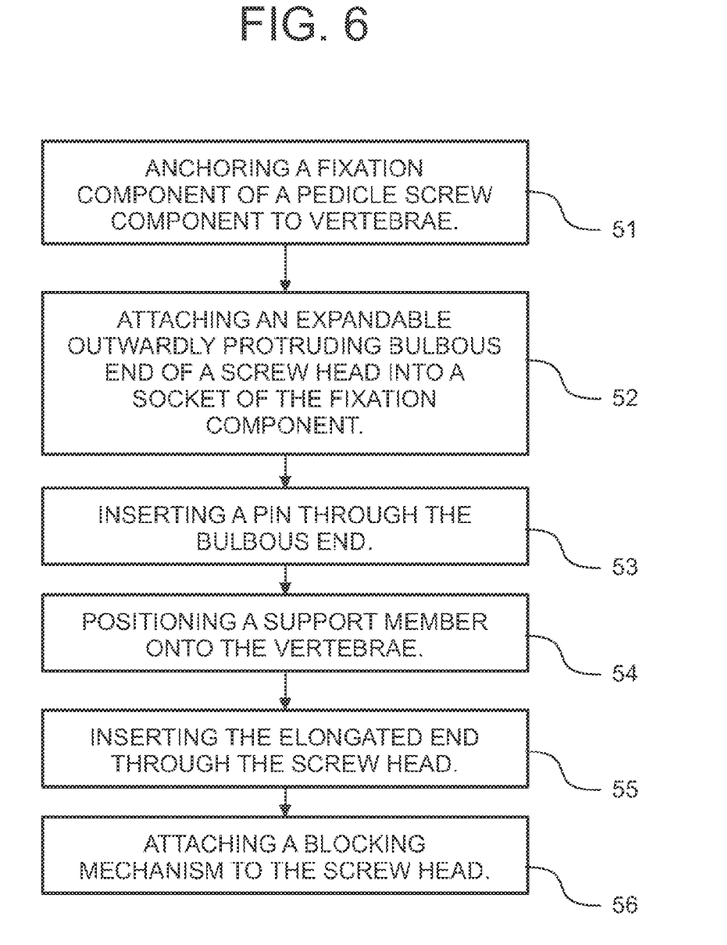
FIG. 6 is a flow diagram illustrating a preferred method according to an embodiment herein.

FIG. 6, with reference to FIGS. 1(A) through 5, is a flow diagram illustrating a method according to an embodiment herein, wherein the method comprises anchoring (51) a fixation component 25 of a pedicle screw component 20 to vertebrae 7, wherein the fixation component 25 comprises a socket 26; attaching (52) an expandable outwardly protruding bulbous end 23 of a screw head 21 into the socket 26; inserting (53) a pin 35 through the bulbous end 23; and positioning (54) a support member 1 onto the vertebrae 7, wherein the support member 1 comprises an elongated end 2 comprising a longitudinal axis X; a hook 3 connected to the elongated end 2 in which the vertebrae 7 is received, wherein the hook 3 is angled in three different planes with respect to the longitudinal axis X; and a connector section 4 that connects the elongated end 2 to the hook 3, wherein the connector section 4 is angled with respect to the elongated end 2 and comprises a thickness less than a thickness of the elongated end 2. The method further comprises inserting (55) the elongated end 2 through the screw head 21; and attaching (56) a blocking mechanism 30 to the screw head 21 to compress the elongated end 2 against the pin 35 causing the bulbous end 23 to outwardly expand and lock into the socket 26, and causing the hook 3 to compress against the vertebrae 7. Additionally, the method may further comprise creating a slot 40 in the vertebrae 7; and attaching the hook 3 in the slot 40. Moreover, the support member 1 may further comprise a ring member 13 encircling the connector section 4, wherein the method may further comprise applying pressure to the ring member 13 and the screw head 21 in order to move the hook 3 closer to the screw head 21.

The embodiments herein provide a device 1 that provides non-fusion treatment for direct repair of the pars defect. The device 1 is configured to be used in conjunction with a monoaxial or polyaxial pedicle screw component 20 to enable compression to the defect site. The hook 3 is configured to prevent lateral slippage. The shape and form of the device may also aid in containing placement of bone graft to the desired area. For a bilateral indication the device 1 may be configured in both left and right sided implant configurations.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A device for fixing a spinal support to vertebrae, said device comprising:
    an elongated end comprising a longitudinal axis;
    a hook, adapted for receiving said vertebra, connected to said elongated end,
        wherein said hook is angled in three different planes with respect to said longitudinal axis, and
        wherein said three different planes are transverse to each other; and a connector section that connects said elongated end to said hook,
  wherein said connector section is angled with respect to said elongated end and comprises a thickness less than a thickness of said elongated end, and
  wherein said hook becomes progressively larger to said connector section.

2. The device of claim 1,
wherein said hook comprises an elbow connector defining a recess for receiving said vertebrae.

3. The device of claim 2, wherein said hook comprises a gripping portion comprising serrated teeth positioned adjacent to said elbow connector.

4. The device of claim 2, wherein said hook comprises a head section having a width greater than a width of each of said elongated end and said connector section.

5. The device of claim 4, wherein any of said elongated end and said head section comprises a hole configured therethrough.

6. The device of claim 4, wherein said head section is angled with respect to said elongated end.

7. The device of claim 4, wherein said elbow connector is angled with respect to said head section.

8. The device of claim 4, wherein said gripping portion is angled with respect to said elbow connector.

9. The device of claim 1, further comprising a ring member encircling said connector section.

10. An apparatus for fixing a spinal support to vertebrae, said apparatus comprising:
  a support member comprising:
    an elongated end comprising a longitudinal axis;
    a hook, adapted for receiving said vertebra, connected to said elongated end, wherein said hook is angled in three different planes with respect to said longitudinal axis; and
    a connector section that connects said elongated end to said hook,
      wherein said connector section is angled with respect to said elongated end and comprises a thickness less than a thickness of said elongated end, and
      wherein said hook becomes progressively larger to said connector section;
  a pedicle screw component comprising:
    a fixation component adapted to be anchored in said vertebrae, wherein said fixation component comprises a socket;
    a screw head comprising:
      an expandable outwardly protruding bulbous end that fits into said socket; and
      a channel that receives said elongated end of said support member;
    a pin positioned through said bulbous end causing outward expansion of said bulbous end; and
    a blocking mechanism attached to said screw head and adjacent to said elongated end of said support member.

11. The apparatus of claim 10, wherein said hook comprises an elbow connector defining a recess for receiving said vertebrae.

12. The apparatus of claim 11, wherein said hook comprises a gripping portion comprising serrated teeth positioned adjacent to said elbow connector.

13. The apparatus of claim 11, wherein said hook comprises a head section having a width greater than a width of each of said elongated end and said connector section.

14. The apparatus of claim 13, wherein said head section is angled with respect to said elongated end.

15. The apparatus of claim 13, wherein said elbow connector is angled with respect to said head section.

16. The apparatus of claim 13, wherein said gripping portion is angled with respect to said elbow connector.

17. The apparatus of claim 10, wherein said support member comprises a hole configured therethrough.

18. The apparatus of claim 10, wherein said support member further comprises a ring member encircling said connector section.

19. A method comprising:
  anchoring a fixation component of a pedicle screw component to vertebrae, wherein said fixation component comprises a socket;
  attaching an expandable outwardly protruding bulbous end of a screw head into said socket;
  inserting a pin through said bulbous end;
  positioning a support member onto said vertebrae, wherein said support member comprises:
    an elongated end comprising a longitudinal axis;
    a hook connected to said elongated end in which said vertebrae is received, wherein said hook is angled in three different planes with respect to said longitudinal axis; and
    a connector section that connects said elongated end to said hook,
      wherein said connector section is angled with respect to said elongated end and comprises a thickness less than a thickness of said elongated end, and
      wherein said hook becomes progressively larger to said connector section;
  inserting said elongated end through said screw head; and
  attaching a blocking mechanism to said screw head to compress said elongated end against said pin causing said bulbous end to outwardly expand and lock into said socket, and causing said hook to compress against said vertebrae.

20. The method of claim 19, further comprising:
creating a slot in said vertebrae; and
attaching said hook in said slot.

21. The method of claim 19, wherein said support member further comprises a ring member encircling said connector section, and wherein said method further comprises applying pressure to said ring member and said screw head in order to move said hook closer to said screw head.

* * * * *